US 7,225,807 B2

(12) United States Patent
Papania et al.

(10) Patent No.: US 7,225,807 B2
(45) Date of Patent: Jun. 5, 2007

(54) SYSTEMS AND METHODS FOR AEROSOL DELIVERY OF AGENTS

(75) Inventors: Mark James Papania, Lilburn, GA (US); James J. Barry, Hanover, NH (US); Nabil A. Elkouh, Meriden, NH (US); Mark C. Bagley, Grafton, NH (US)

(73) Assignees: Creare Incorporated, Hanover, NH (US); The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 515 days.

(21) Appl. No.: 10/471,620

(22) PCT Filed: Mar. 13, 2002

(86) PCT No.: PCT/US02/07973

§ 371 (c)(1),
(2), (4) Date: Feb. 23, 2004

(87) PCT Pub. No.: WO02/074372

PCT Pub. Date: Sep. 26, 2002

(65) Prior Publication Data

US 2004/0134494 A1    Jul. 15, 2004

Related U.S. Application Data

(60) Provisional application No. 60/276,539, filed on Mar. 15, 2001.

(51) Int. Cl.
*A61M 15/00* (2006.01)
*A61M 16/10* (2006.01)
*A61M 16/00* (2006.01)
*A61M 15/08* (2006.01)
*A61M 11/00* (2006.01)
*F16K 11/00* (2006.01)
*G05D 11/02* (2006.01)

(52) U.S. Cl. .................... 128/203.12; 128/204.12; 128/203.25; 128/200.14

(58) Field of Classification Search ........... 128/203.12, 128/203.14, 203.25, 200.22, 205.24, 200.14, 128/200.16, 200.18, 200.21
See application file for complete search history.

(56) References Cited

U.S. PATENT DOCUMENTS 318,930 A * 5/1885 Sutton .................... 128/200.14

(Continued)

FOREIGN PATENT DOCUMENTS

DE    40 19 656 A1    3/1991

(Continued)

OTHER PUBLICATIONS

Holzner et al., "Characterization of Particle Size and Microbiological Properties of a Novel Low Frequency Ultrasonic Nebulizer," Proc. 2nd World Meeting APGI/APV, Paris, May 25-28, 1998, pp. 953-954.

(Continued)

*Primary Examiner*—Justine R. Yu
*Assistant Examiner*—K C Matter
(74) *Attorney, Agent, or Firm*—Klarquist Sparkman, LLP

(57) ABSTRACT

Aerosol delivery systems and methods for delivering an agent to a patient are described herein. The present invention includes embodiments comprising an insulated receptacle connected to a body to hold a vial of an agent to be delivered to a patient. The vial is located in an inverted position within the receptacle and connected to the housing. One or more reusable thermal packs can be located on the inner sides of the receptacle, to maintain a selected temperature surrounding the vial. The agent is administered to a patient by placing a prong into one of the patient's orifices and then activating an aerosol delivery system. Such systems comprise jet aerosolization and pneumatic and ultrasonic nebulizers and preferably are portable.

33 Claims, 8 Drawing Sheets

U.S. PATENT DOCUMENTS

| | | | |
|---|---|---|---|
| 2,908,479 A * | 10/1959 | Goodspeed, Jr. ............. | 251/320 |
| 3,861,386 A | 1/1975 | Harris et al. | |
| 4,036,223 A | 7/1977 | Obert | |
| 4,106,503 A | 8/1978 | Rosenthal et al. | |
| 4,117,844 A * | 10/1978 | James .................... | 128/203.15 |
| 4,286,636 A * | 9/1981 | Credle ........................ | 141/114 |
| 4,319,155 A | 3/1982 | Nakai et al. | |
| 4,756,347 A * | 7/1988 | Hagan et al. ................ | 141/21 |
| 4,877,989 A | 10/1989 | Drews et al. | |
| 5,063,922 A | 11/1991 | Häkkinen | |
| 5,215,079 A | 6/1993 | Fine et al. | |
| 5,261,601 A | 11/1993 | Ross et al. | |
| 5,443,059 A | 8/1995 | Koch et al. | |
| 5,499,972 A | 3/1996 | Parsons | |
| 5,515,841 A | 5/1996 | Robertson et al. | |
| 5,515,842 A * | 5/1996 | Ramseyer et al. ..... | 128/200.14 |
| 5,544,646 A | 8/1996 | Lloyd et al. | |
| 5,551,416 A | 9/1996 | Stimpson | |
| 5,660,166 A | 8/1997 | Lloyd et al. | |
| 5,704,911 A | 1/1998 | Parsons | |
| 5,709,202 A | 1/1998 | Lloyd et al. | |
| 5,758,637 A | 6/1998 | Ivri et al. | |
| 5,803,362 A | 9/1998 | Fraccaroli | |
| 5,826,571 A | 10/1998 | Casper et al. | |
| 5,848,587 A | 12/1998 | King | |
| 5,879,327 A | 3/1999 | Moreau DeFarges et al. | |
| 5,891,086 A | 4/1999 | Weston | |
| 5,921,232 A | 7/1999 | Yokoi et al. | |
| 5,950,619 A | 9/1999 | van der Linden et al. | |
| 5,970,974 A * | 10/1999 | Van Der Linden et al. ...................... | 128/200.14 |
| 5,996,903 A | 12/1999 | Asai et al. | |
| 6,026,807 A * | 2/2000 | Puderbaugh et al. ... | 128/200.14 |
| 6,116,237 A | 9/2000 | Schultz et al. | |
| 6,125,844 A * | 10/2000 | Samiotes ............... | 128/200.12 |
| 6,158,431 A | 12/2000 | Poole | |
| 6,196,218 B1 | 3/2001 | Voges | |
| 6,196,219 B1 | 3/2001 | Hess et al. | |
| 6,273,342 B1 | 8/2001 | Terada et al. | |
| 6,363,932 B1 * | 4/2002 | Forchione et al. ..... | 128/200.14 |
| 6,550,472 B2 * | 4/2003 | Litherland et al. ..... | 128/200.14 |
| 6,651,650 B1 | 11/2003 | Yamamoto et al. | |
| 6,676,034 B2 | 1/2004 | Tanaka et al. | |
| 6,851,626 B2 | 2/2005 | Patel et al. | |
| 2002/0124852 A1 | 9/2002 | Gonda et al. | |
| 2002/0195100 A1 * | 12/2002 | Webb .................... | 128/200.14 |
| 2003/0164169 A1 | 9/2003 | Stangl et al. | |
| 2004/0055596 A1 * | 3/2004 | Bacon ................... | 128/200.12 |
| 2005/0011514 A1 | 1/2005 | Power et al. | |
| 2005/0199236 A1 | 9/2005 | Fink et al. | |
| 2005/0205089 A1 | 9/2005 | Fink et al. | |

FOREIGN PATENT DOCUMENTS

| | | |
|---|---|---|
| EP | 0 646 385 A1 | 4/1995 |
| EP | 1 149 602 | 10/2001 |
| EP | 0701457 | 12/2003 |
| JP | 061068159 | 4/1986 |
| JP | 07080369 | 3/1995 |
| JP | 08196965 | 8/1996 |
| JP | 2000233158 | 8/2000 |
| JP | 2001149473 | 6/2001 |
| JP | 2001149833 | 6/2001 |
| JP | 2001149834 | 6/2001 |
| WO | WO 00/58022 | 10/2000 |

OTHER PUBLICATIONS

Cutts et al., "Alternative Routes of Measles Immunization: a Review," *Biologicals* 25(3):323-338 (1997).

Dixon, "Sound Medicine," *British Medical Journal (International)* 311:1030 (1995).

Dhand, "Nebulizers that Use a Vibrating Mesh or Plate with Multiple Apertures to Generate Aerosol," *Respir. Care* 47:1406-1416 (2002).

Greenspan B.J., "Ultrasonic and Electrohydrodynamic Methods for Aerosol Generation," in Hickey, AJ, ed., *Inhalation Aerosols: Physical and Biological Basis for Therapy*, New York, Marcel Dekker, Inc., 1996.

Grossman J., "The Evolution of Inhaler Technology," *J. Asthma* 31:55-64 (1994).

Harvey et al., "Comparison of Jet and Ultrasonic Nebulizer Pulmonary Aerosol Deposition During Mechanical Ventilation," *Eur. Respir. J. 10*:905-909 (1997).

Lefebvre, A.H., *Atomization and Sprays*, New York, Hemisphere, 1989.

Niven, R. W., Atomization and Nebulizers, in Hickey, A.J., ed., *Inhalation Aerosols: Physical and Biological Basis for Therapy*, New York, Marcel Dekker, Inc., 1996.

Drug Delivery Systems—Pulmonary: Part 5, in *Medical & Healthcare Marketplace Guide*, v. 1, p. I-376+, 1998).

The International Search Report and the Written Opinion of the International Searching Authority of PCT Application No. PCT/US2005/011086.

\* cited by examiner

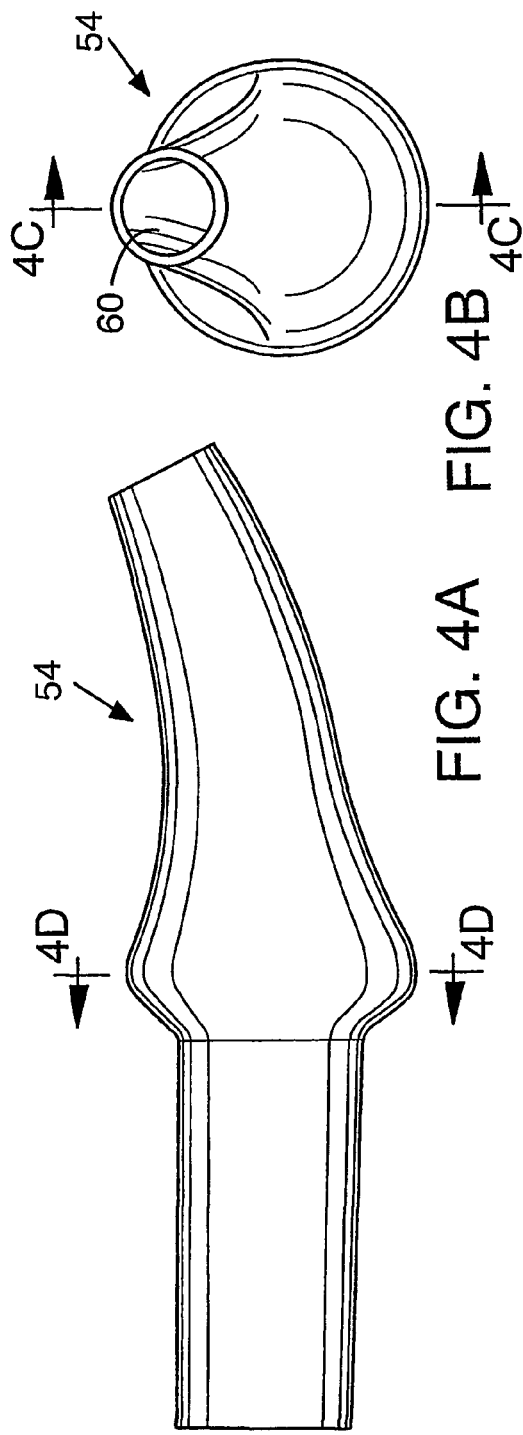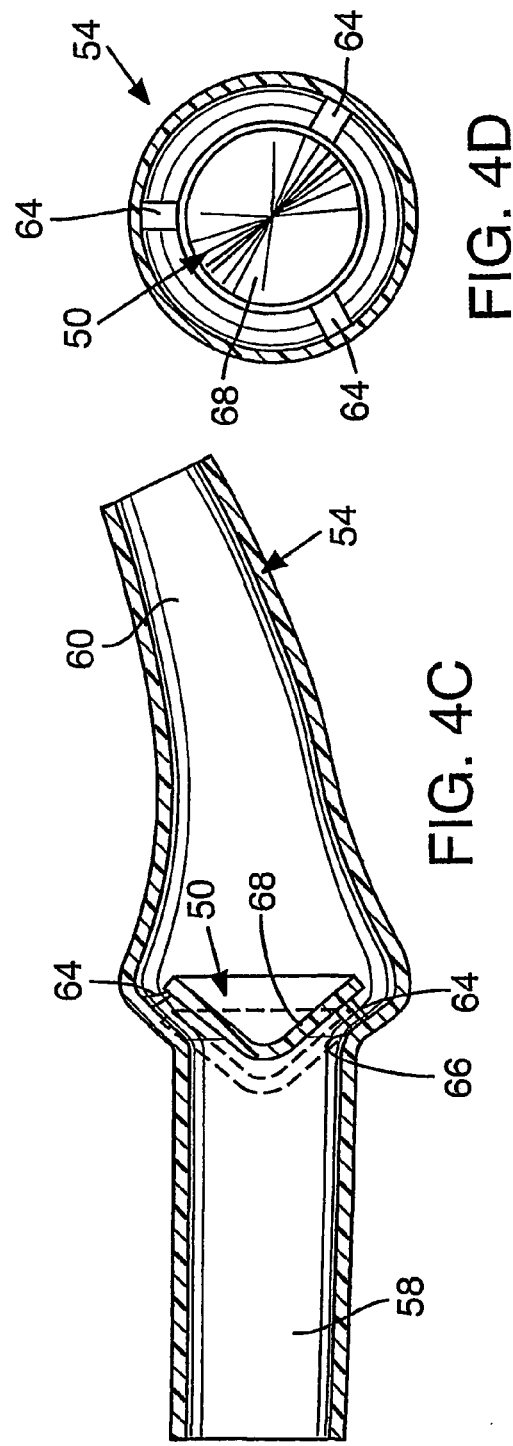

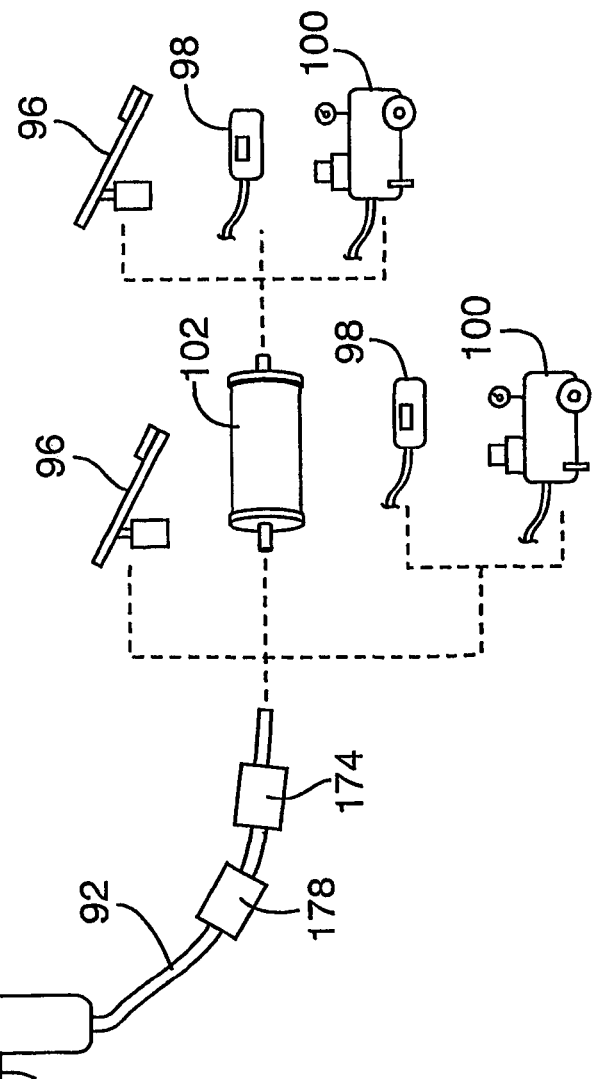
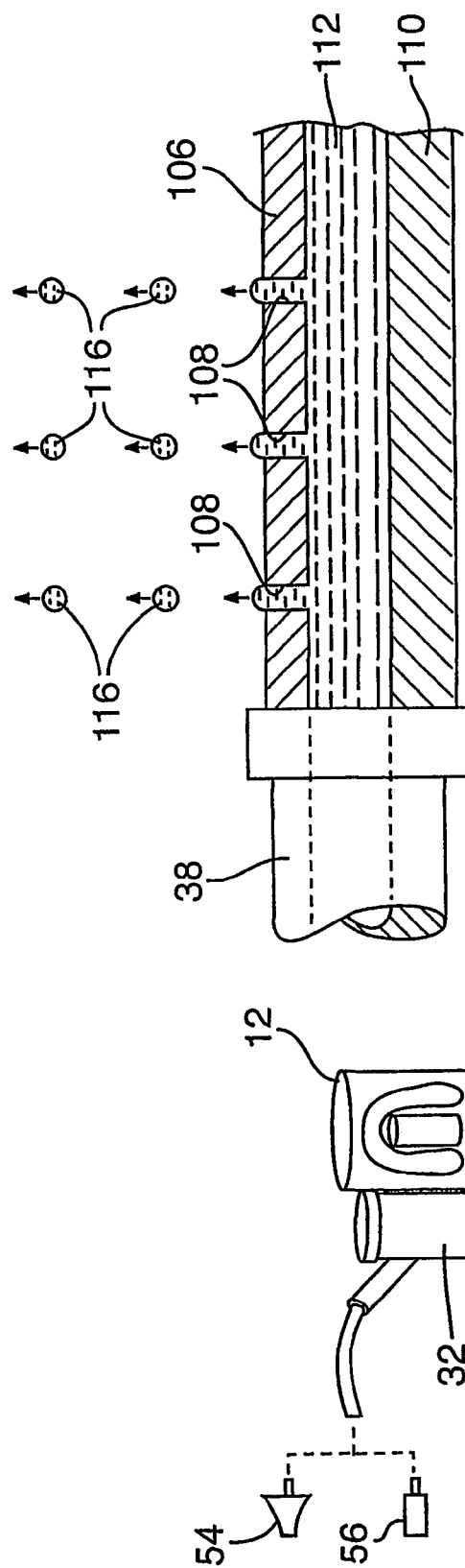
FIG. 6
FIG. 7

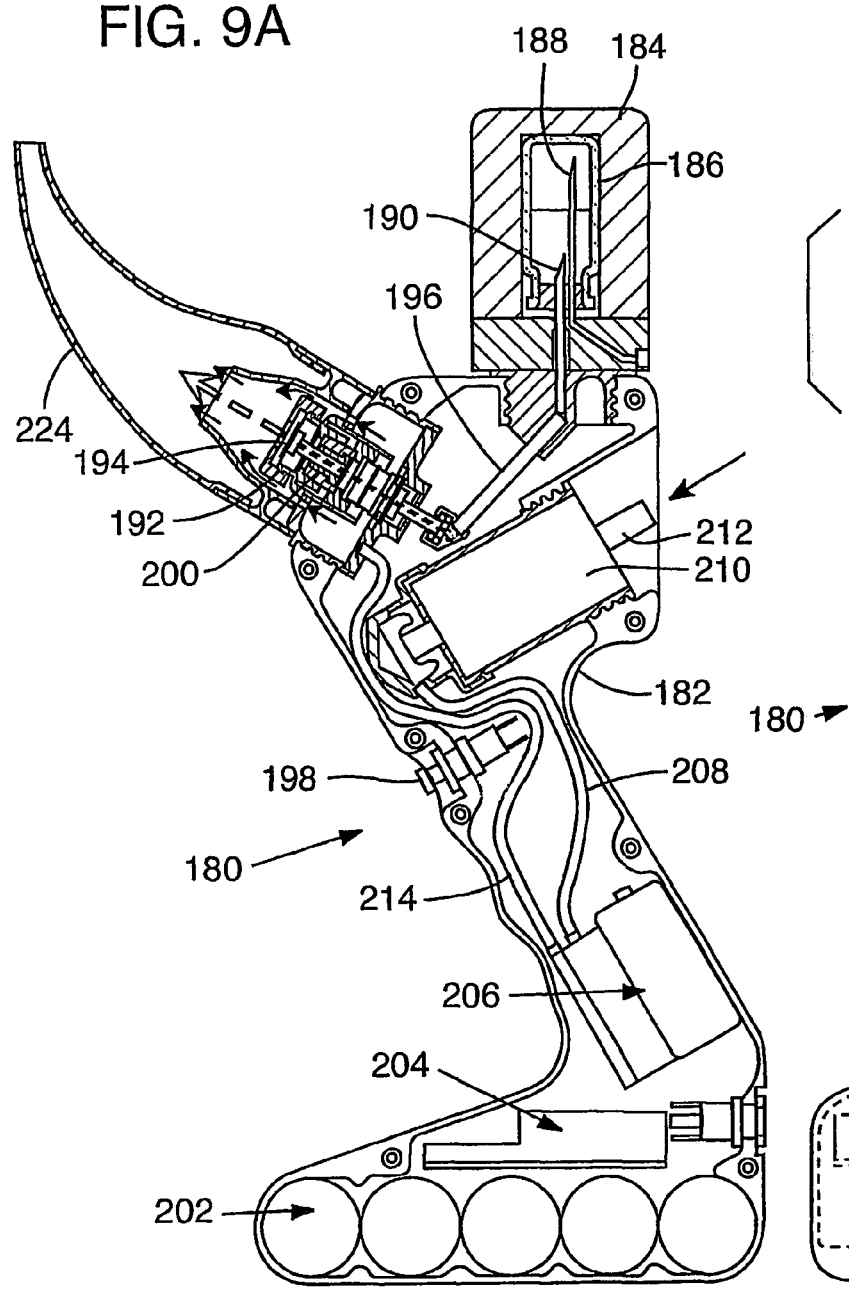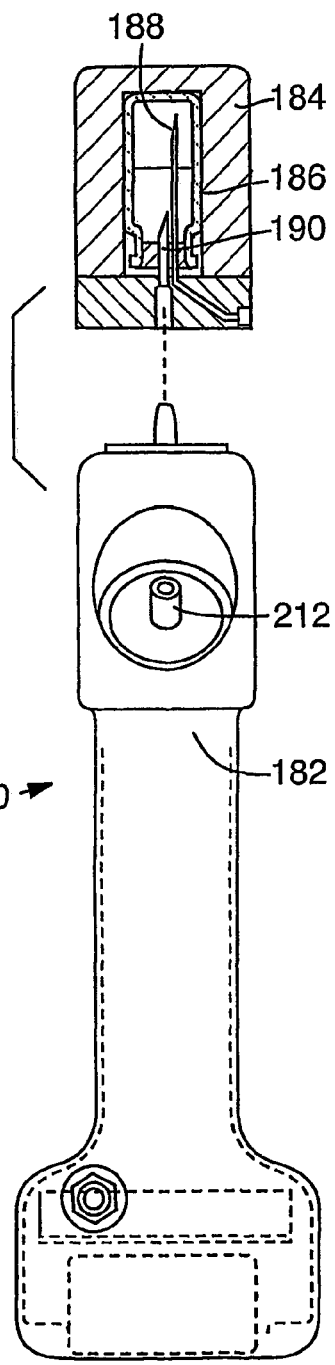

SYSTEMS AND METHODS FOR AEROSOL DELIVERY OF AGENTS

This is a national stage under 35 U.S.C. §371 of International Application No. PCT/US02/07973, filed Mar. 13, 2002, and claims the benefit of U.S. Provisional Patent Application No. 60/276,539, filed Mar. 15, 2001.

FIELD OF THE INVENTION

This disclosure relates generally to the delivery of agents, and more particularly, to systems and methods for delivery of agents using portable aerosol devices.

BACKGROUND

Medicines and other agents have been administered with needles and syringes for many years. Needles and syringes have posed a variety of problems for patients and medical personnel who administer agents to the patients, including injection safety, needle stick injury, disposal problems, transmission of blood borne diseases, and needle shortages during mass vaccination campaigns. The replacement of needles and syringes as the primary delivery vehicle for agents has the potential for tremendous cost savings, increased safety and reduction of biomedical wastes.

Currently there exist at least three methods for administration of agents using pulmonary delivery devices, including; nebulizers, metered dose inhalers, and dry powder inhalers. Much of the equipment used for aerosol delivery is cumbersome and has not been widely employed for many treatment methods. Nebulizers are commonly used in hospitals for the treatment of respiratory diseases. In practice, a nebulizer uses compressed gases to convert a solution of the agent into fine droplets. The droplets are administered to the patient through an air stream that the patient breathes inwardly through a mouthpiece or mask. As the patient breathes, the agent is delivered to the patient's lungs and absorbed therein.

Typically, nebulizers rely upon an external compressed gas source to convert a solution of the agent into fine droplets. As a result of the need for an external source of compressed gas, nebulizers tend to be bulky and difficult to move. Further, the effectiveness of a nebulizer depends upon proper inhalation by the patient, which can be difficult to monitor and to teach to the patient.

Additionally, nebulizers fall short of an adequate design because they fail to provide a consistent, uniform droplet size. Instead, nebulizers produce a wide range of droplet sizes, often with the droplet size being too large for lung absorption. Thus, the patient either gets less of the agent than is necessary or the nebulizer must administer more of the agent than is necessary so that at least an effective amount will be delivered to the patient. With such methods, the agent is wasted and there is a risk that the patient will inhale too much of the agent and be overdosed.

Currently used jet nebulizers function in the same general way. Liquid is drawn up to an air nozzle by capillary forces and/or the Bernoulli effect. At the nozzle, a high-speed air jet shatters the liquid into droplets. Droplets blast against an impactor to break them up further into smaller droplets. Like most atomization processes, this droplet generation process results in a size distribution. To obtain the desired small aerosol droplets, baffles capture large droplets (which cannot follow the airflow path well), leaving the fine aerosol in the output stream of the nebulizer. The larger droplets recycle to the liquid reservoir of the nebulizer.

This nebulization process is inherently inefficient. Measurements show that typical nebulizers only convert about 1% of the aspirated liquid to fine aerosol droplets. Thus, liquid will normally be recycled well in excess of twenty times before it reaches the desired size and is exhausted from the nebulizer. The inefficiency of the jet nebulizer poses problems to its use for aerosol vaccination. High velocity is needed in the air jet to provide the energy required to break the liquid into sufficiently small droplets, necessitating relatively high air supply pressures in flow rates. Compressing air to provide this supply requires significant power, either human or electric.

Fluid recycling in the nebulizer in the small amount of vaccine required for each dose results in the inability to operate on a dose-by-dose basis. Many doses need to be present in the nebulizer in order for droplet coalescence on the baffles in other surfaces to return liquid to the reservoir. In addition, the repeated mechanical stress of atomization on the vaccination particles in the liquid risks diminishing the viability of the vaccine.

Further compounding the inherent problems found in prior nebulizer design is the required duration of drug administration. Typically, nebulizers require several minutes of use to administer a proper drug dosage. Accordingly, the patient is required to maintain the desired breathing technique throughout the application period. Even so, such precision by the patient is seldom found in practice. Therefore, such nebulizers are inefficient and impractical drug delivery devices.

Another system for delivering an agent is a metered dose inhaler (MDI). MDI represents the most widely used system for pulmonary delivery of agents, especially pharmaceuticals, and consists in part of a canister which holds the agent, together with a propellant, typically a chlorofluorocarbon (CFC). A patient may self-administer the agent by activating the canister, thereby releasing a high velocity air stream consisting of a mixture of air and the agent. As with the nebulizers, MDI's produce a wide range of droplet sizes; however, only a small portion of the droplets produced are absorbed by the patient.

Administration of the agent is effective only if the patient coordinates inhalation with activation of the canister. Problems arise if the patient fails to coordinate inhalation with the release of the agent by the canister. Specifically, the agent can be deposited at the back of the throat, rather than on the interior walls of the lungs, thereby causing the agent to be ingested, digested and expelled from the patient rather than being absorbed directly by the bloodstream or being effective on site in the lungs. Although spacer devices have been developed to overcome the difficulty of press-and-breathe coordination, problems still exist with the inhalation technique and compliance monitoring. Accordingly, MDI's have not proved to be an effective system of pulmonary delivery.

Additionally, MDIs suffer from the reliance on a propellant. Chlorofluorocarbons have long been the propellant of choice, and these compounds have severe environmental consequences. Thus, the use of chlorofluorocarbons are being phased out. The replacement propellants may not be as safe or effective for pulmonary delivery devices.

Still another method of pulmonary or inhalant delivery is the dry powder inhaler (DPI), introduced to the marketplace as a replacement for the MDI systems, particularly to overcome the need for a chlorofluorocarbon propellants. A DPI uses a portable canister that stores an agent in a dry powder state. Patients can self-administer the agent by inhaling small, dry particles. Unlike other methods of pulmonary delivery, agents used with DPI's must be prepared as a solid, must be able to tolerate storage in a solid phase, and must be capable of complete dispersion at the point of delivery. As a result, many agents are not compatible for use with the DPI method of delivery. Accordingly, DPI's may be an ineffective method of delivery of agents.

Thus, a need exists for effective systems and methods for administering an agent in an aerosol form, without a needle, and in more accurate dosages. Further, a need exists for portable delivery systems that provide an agent to patients in a form that may be rapidly absorbed.

SUMMARY OF THE DISCLOSURE

The present disclosure comprises methods and systems for delivery of agents that do not require use of needles to gain entry into a biological system. More particularly, the present disclosure comprises methods and systems of delivery of agents using portable devices comprising pneumatic, ultrasonic or jet aerosol methods. For example, such systems and methods can be used for delivering agents such as pharmaceuticals, chemotherapeutics, immune agents, and vaccines. Preferred embodiments of the present disclosure overcome problems of other devices that rely on external air sources or power supplies.

An embodiment of the present disclosure provides methods and systems for administering one or more agents to multiple patients (either human or non-human) in single dosage applications or to an individual patient for multiple administrations. For example, many patients can be immunized with an inhaled vaccine composition using the present disclosure without the need for needles or reloading of the device with the composition. In other applications, the composition may be administered to one individual. For example, only a single vaccine or drug dose is administered using aerosol administration methods of the present disclosure while the remainder of the vaccine or drug remains unaffected in the vial.

Preferred embodiments of the present disclosure insulate the agent so that it is not adversely affected by outside temperature during administration or storage. Furthermore, the present disclosure comprises embodiments that allow control of an air and agent mixture in order to insure that a patient receives a predetermined dose of the agent. Moreover, the present disclosure comprises embodiments that provide a portable power source that can be self-contained within the device.

An embodiment of the present disclosure comprises the following example. A preferred method comprises administration of a vaccine composition using the devices of the present disclosure. For example, the device comprises an insulated housing connected to a body defining a vial. The vial is designed to contain a vaccine or drug composition. The vial is located in an inverted position within the body and connected to the housing. A cooling means, such as one or more replaceable ice packs, can be located on the inner sides of the insulated housing to reduce or maintain the ambient temperature surrounding the vial. The vaccine composition is delivered to the recipient's airway using pneumatic, ultrasonic or jet propulsion means and devices.

The present disclosure comprises systems and devices comprising aerosol generation means and power sources, and may further comprise fluid recycling of the compositions to be delivered and positive pressure output Preferred embodiments comprising pneumatic and ultrasonic means generally employ aerosol generation means comprising direct microdrilled surfaces, whereas jet aerosol embodiments preferably comprise air blast atomization. Power sources employed by the present disclosure preferably comprise compressed air or electrical means.

Preferred methods of the present disclosure comprise delivering agent compositions by placing a prong into one of the patient's nares and then activating the aerosol delivery system. For example, when an external trigger is depressed, the system converts the agent composition into numerous droplets. Preferably, the droplet composition is mixed with air and transported from the delivery system through a prong into the patient's naris.

In one aspect of the disclosure, a timer controls the droplet formation of the agent composition. The timer can initiate a signal for the droplet formation to cease, and a valve is controlled to allow air to be released from the air reservoir. If it is desired that another dose be administered, a second dose can be delivered from the vial into a mixing chamber upon depression of the external trigger.

In yet another aspect of the disclosure, preferred ultrasonic embodiments include an electronic drive powered by rechargeable batteries. The batteries may be recharged by means known to those skilled in the art, including the use of a hand-cranked dynamo and/or an associated AC power converter. The dynamo and associated AC power converter can be separate or self-contained within the system.

Another aspect of the present disclosure comprises embodiments wherein only one dose of the agent composition is mixed with air and delivered to the patient, thereby protecting the remainder of the agent composition in the vial from degradation due to any heat or other deleterious effects produced during the delivery process.

Another aspect of this disclosure is the use of replaceable or reusable form fitting cold packs rather than ordinary ice to maintain the temperature of the agent composition while it is stored in the vial.

Still yet another aspect of this disclosure is the use of a prong for accurately directing the agent composition mixture into the patient's orifices, such as the mouth or the nares, for administration to the patient for effective treatment.

Yet another aspect of preferred embodiments of the present disclosure is the use of an anti-backflow valve to prevent contamination of the system by configuring the prong and valve so that a straight path from the prong outlet through the valve does not exist.

Still another aspect of the present disclosure is the incorporation of a positive pressure air source within the delivery system.

As the following description and accompanying drawings make clear, these and other aspects or objects are achieved by the present disclosure.

BRIEF DESCRIPTION OF THE DRAWINGS

FIGS. 4A and 4B are side and end views, respectively, of a prong for a jet aerosol agent delivery system.

FIG. 4C is a section view taken generally along line 4C—4C in FIG. 4B and FIG. 4D is a section view taken generally along line 4D—4D in FIG. 4A.

FIG. 6 is an enlarged illustration of portions of an orifice plate and actuator for use in a pneumatically activated aerosol generator embodiment of the present disclosure as shown in FIG. 5C.

FIG. 7 depicts a schematic diagram of alternative embodiments of the present disclosure.

FIGS. 9A and 9B illustrate a sectional side view and end view, respectively, of another embodiment of the present disclosure.

DETAILED DESCRIPTION OF EMBODIMENTS

Figure 1:
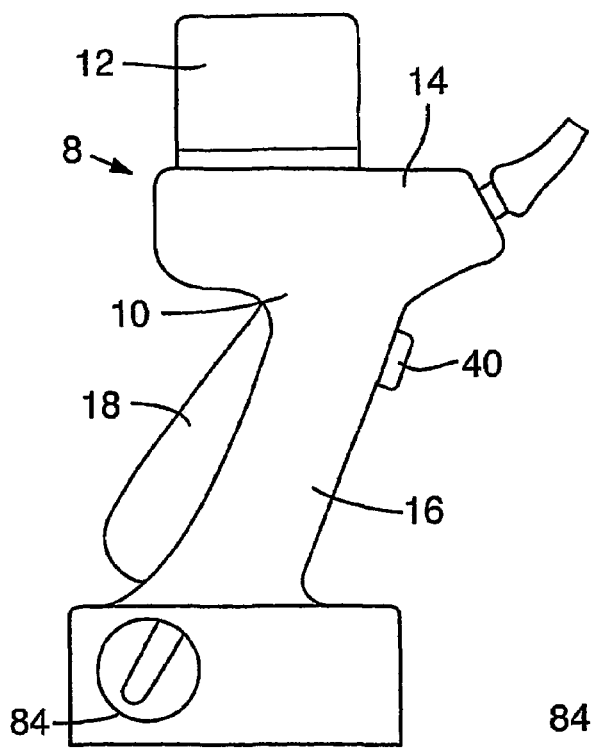
FIG. 1 illustrates a side view of an embodiment of the present disclosure.

The present disclosure is directed to methods and systems, including devices, for delivery of agents, preferably by aerosol delivery. Preferred systems for such delivery comprise jet nebulizer systems, pneumatic and ultrasonic aerosol generation systems. Preferred methods comprise administration of agents for treatment of living organisms, such as for methods of vaccination.

Use of the present system for agent delivery, such as for vaccination purposes, provides many benefits. The present system replaces the use of needles and syringes, and reduces the costs of agent delivery. Additionally, the present system allows for treatment of patients by less-trained staff, another cost saving benefit, and also helps prevent the spread of blood borne diseases by reused needles.

The aerosol delivery systems and methods of the present system are capable of providing agents in a continuous aerosol stream at a steady flow rate, may or may not need electrical power, are portable, and have a replaceable prong. For vaccination purposes, many of the embodiments may keep up to 100 doses of vaccine at a selected temperature, (for example around 9° C.) for up to 8 hours, and employ a trigger mechanism to draw a selected dose from such storage and deliver that dose. Additionally, the devices of the present system can be used to deliver from 1 to 500 doses an hour, preferably 1 to 250 doses an hour, and more preferably 1 to 100 doses per hour. The devices also provide a non-threatening appearance to reduce fear of treatment in patients. It is preferable that the systems and devices are easy to disassemble and clean.

Preferred methods of the present disclosure comprise delivery of agents such as vaccine compositions. The methods of the present disclosure comprise delivery of vaccine compositions via aerosol administration. The present disclosure contemplates the use of any vaccine composition that can be delivered via aerosol administration. Particularly preferred vaccination compositions are those for measles, mumps and rubella. Such compositions may comprise measles vaccine, mumps vaccine, rubella vaccine and combinations and mixtures such as measles and mumps, rubella and mumps, measles and rubella, and measles, mumps and rubella. The vaccines further comprise pharmaceutical or formulation components such as those known in the art, including, but not limited to, diluents, compounding agents, surfactants, and agents to maintain sterility.

Aerosol administration takes advantage of the benefits of such administration. The respiratory system, including the lungs, provides for a large surface area for absorption or adsorption of agents, and can be used for localized or systemic treatment of the recipient.

Agents, as used herein, comprise agents that can be administered to living organisms for an effect in the treated organism. Such agents include live and killed organisms for vaccination, immunogens, immune activators or suppressors, chemotherapeutics, pharmaceuticals, nucleic acids, insulin, hormones, antibodies and fragments thereof, receptors, proteins, carbohydrates, fats, nutrients, anesthetics, narcotics, and pain relievers.

Figure 2:
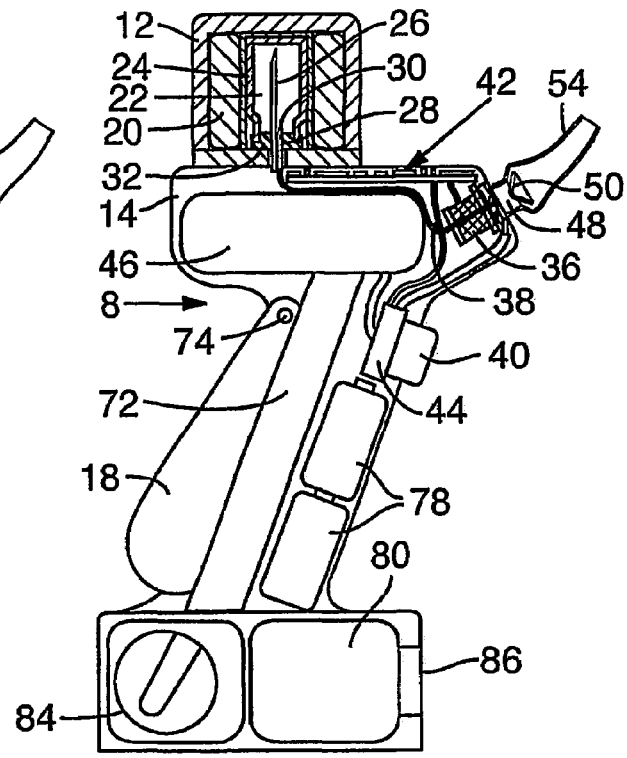
FIG. 2 depicts a section view of an embodiment of the delivery system comprising an ultrasonic system.

FIGS. 1 and 2 show two views of an embodiment of an ultrasonic delivery system which uses direct droplet generation, such as using a piezoelectric-driven actuator to eject droplets. The hand-held device can be operated by various power systems, including a wind-up power supply such as a muscle recharged battery used in portable radios, to operate the ultrasound electronics. Standard electrical supplies can also be used, including batteries, AC power sources, DC power sources, or solar power. Such systems may also comprise a bayonet-mounted cold pack and a disposable prong that prevents contamination by backflow.

In operation, to provide a positive-air supply, the user squeezes a handle in the grip of the device prior to administering each dose to fill the air reservoir. On triggering of a dose, air is delivered along with the aerosolized agent via the prong, into the treated organism or patient. The air dose helps transport the agent into the respiratory tract of the treated organism or patient. It also enables sealing of the device at the base of the prong reducing the risk for unintended release of aerosol if the prong valve is closed, since openings for entrained air are not required. The air dose deliverable by this system preferably will be relatively small, from 50 to 200 cc, more preferably 100 cc, to make the grip-actuated charging pump feasible. If a larger air dose is required, a more substantial air supply can be used with the present system.

FIGS. 3, 5A–5C and 6 illustrate the design of a hand-held aerosol delivery device comprising a pneumatic aerosol generator and components thereof. A plate drilled with many small orifices ejects the droplets on each stroke of a piston actuator. FIG. 6 shows a more detailed example of an operating portion of such a system. A compressed air source powers a pneumatic oscillator to drive the actuator. Exhaust air from the oscillator carries the aerosol away and provides a positive-pressure output stream. A bayonet-mounted cold pack contains the agent and helps to maintain it at a low temperature during administration of multiple doses. The device delivers a dose of agent upon each pull of a trigger. A disposable prong with an integral anti-backflow valve prevents contamination due to sneezes or other events by the treated organism.

Figure 5A:
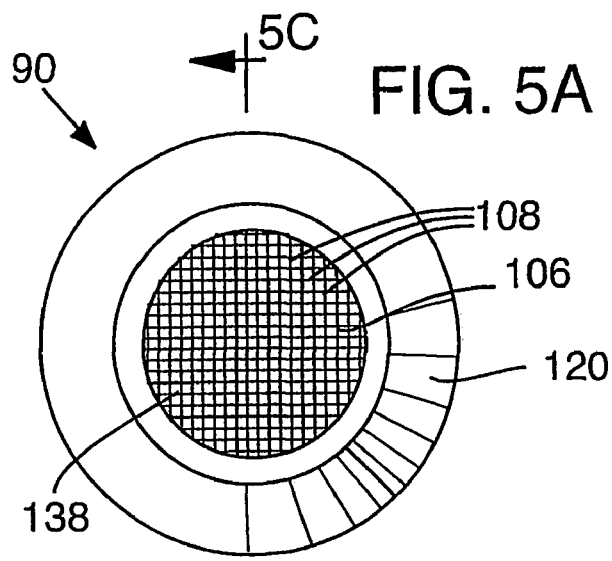
FIGS. 5A–5B illustrate top and side views of an embodiment of the present disclosure comprising a pneumatic aerosol generator.
Figures 5B, 5C:
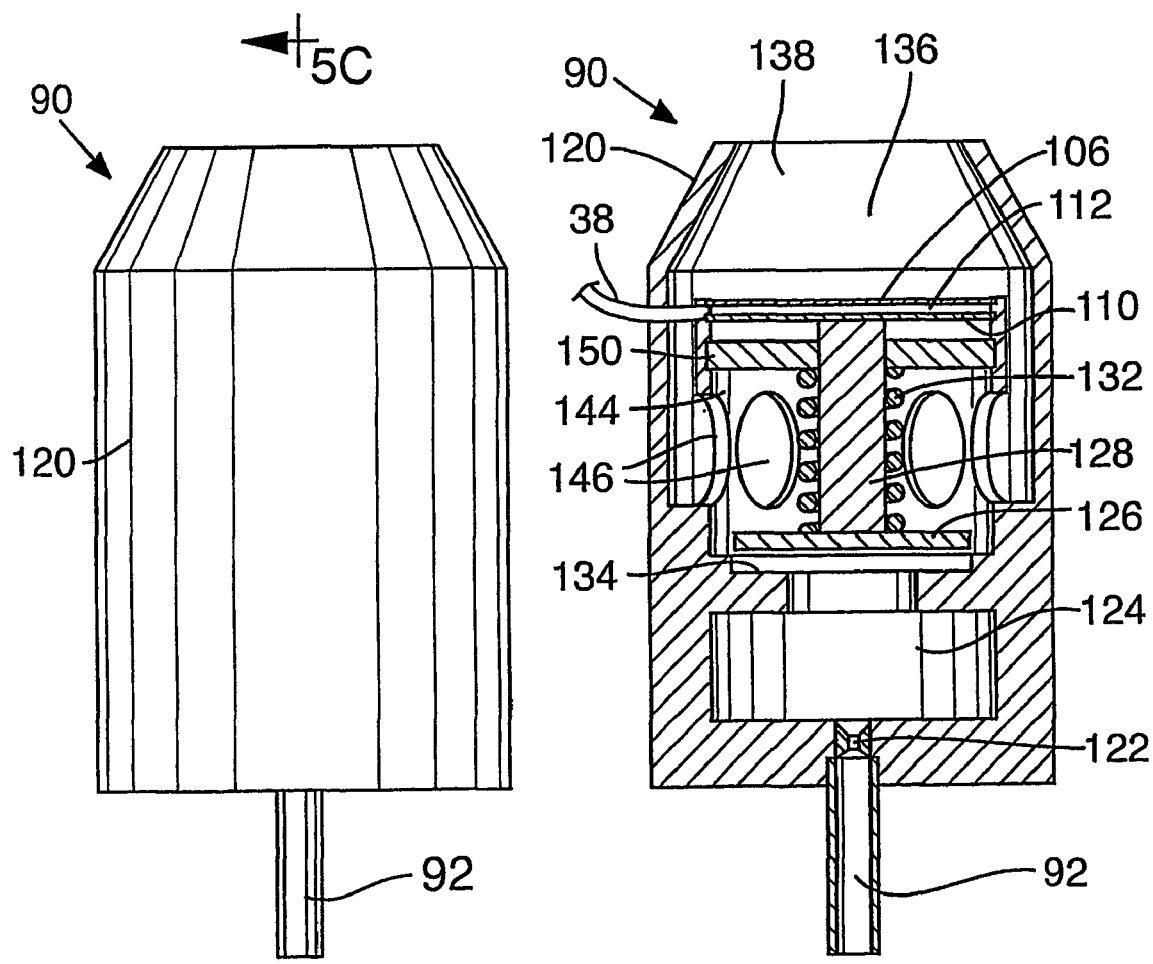
FIG. 5C is a cross-sectional view taken generally along line 5C—5C in FIG. 5A.

FIGS. 5A–5C show an embodiment of a pneumatic aerosol generator. The generator comprises a pneumatic oscillator, a microdrilled orifice plate for direct droplet generation and flow passages for the agent, air and output stream. Air from storage tanks or a compressor enters the oscillator. The area and spring rate of a poppet valve, or piston, in the system are balanced so that the valve behaves unstably, shuttling back and forth, or reciprocating, from a closed to an open position. The valve stem strikes a piston, or actuator, to provide the pressure pulse needed to eject droplets from the orifice plate. Exhaust air from the poppet valve is ducted to entrain the aerosol droplets and carry them out under positive pressure to the prong.

The prong of the present device preferably is disposable and intended to fit easily into the orifices of the treated organism, such as the mouth or naris of the treated organism, to introduce the aerosol and to prevent contamination of the aerosol generator by sneezing or other forceful exhalation by the treated organism.

FIGS. 4–4D show a preferred embodiment of a prong incorporating an anti-backflow valve. An inverted cone provides the moving valve element. Flexible supports, or biasing members, shown here as leaf springs, suspend the element within the valve body, holding it in the open position during normal flow and allowing it to seat to halt backflow. Varying the width and thickness of the supports controls the sensitivity of the valve. The base line support design automatically returns the valve to the normally open position when backflow ceases, but the present system contemplates other design modifications so that the valve could remain in the closed position until reset.

Multiple barriers to backflow contamination are provided by the present disclosure. One of these comprises the moving valve. Other barriers to contamination include the length of the forward portion of the prong, which provides a clean buffer of air against contaminants that could leak around the valve while it is closing. During normal flow, clean air and aerosol flow through the prong and fill it up until the start of backflow. It is the clean air and aerosol in a prong body that rush backward to close the valve as contaminated flow begins to enter at the exit of the prong, preventing contamination during valve closure. Additionally, the prong body and valve elements are shaped so that a straight path from the exit of the prong through the valve does not exist. This prevents contamination by a forceful ejection of a high-speed droplet from the treated organism into the prong. The angled tip of the prong provides one barrier and the design of the valve provides another. Fine aerosols that travel with the air stream can negotiate these paths, but larger high-speed ejection droplets will be captured by the walls and will not reach the aerosol generator.

Such a pneumatic system has several advantages. No recycling of fluid occurs during aerosolization and eliminates the need for a large fluid inventory or multiple exposures of the agent to mechanical stress. The positive-pressure output stream provides forced flow of aerosol that minimizes the need for cooperation of the patient for controlled inhalation. In a preferred embodiment, the device is compact and does not need electricity for operation. Compressed air provides the power to operate the system.

The compressed air can be provided in any means known to those skilled in the art. For example, a pneumatic system may use the modular air supply shown in FIG. 8C. For maximum mobility, compressed air can be stored in one or two backpack mounted tanks. The person providing treatment can then use the hand-held delivery system while on the move with only a single slim air hose connected to the backpack. In stationary use, the hand-held unit can be connected to a compressor or an air supply such as those delivered through wall units in hospital settings.

Figure 8A:
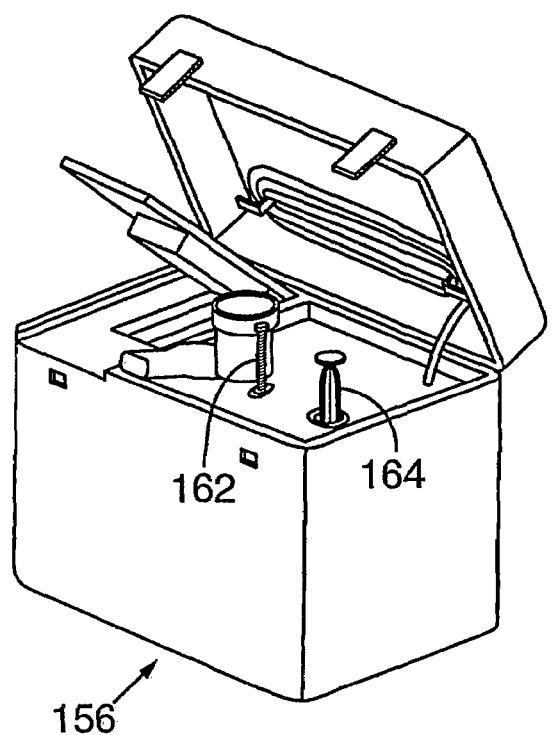
FIGS. 8A–8C illustrate components of an alternative embodiment of the present disclosure for use in a large scale or mass immunization procedure.
Figure 8B:
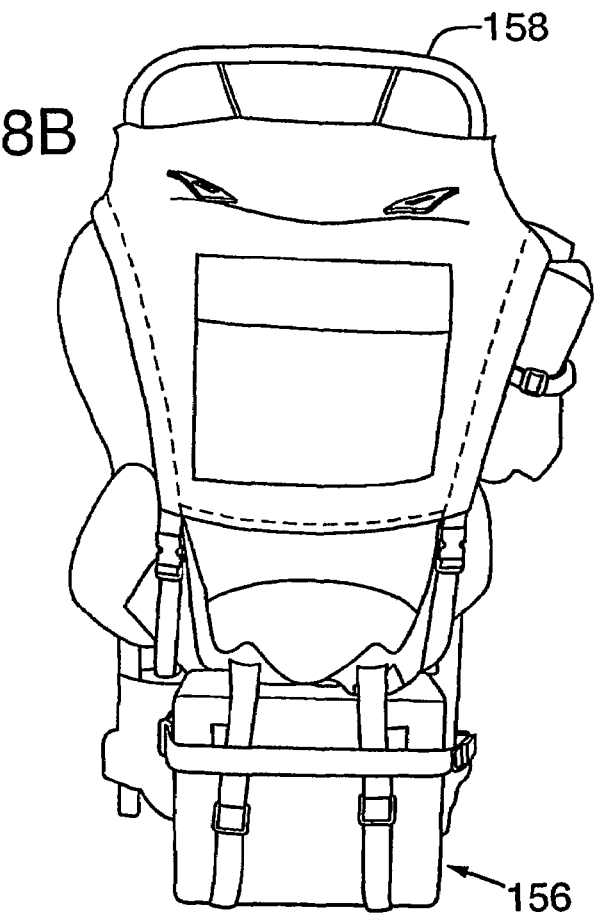
Figure 8C:
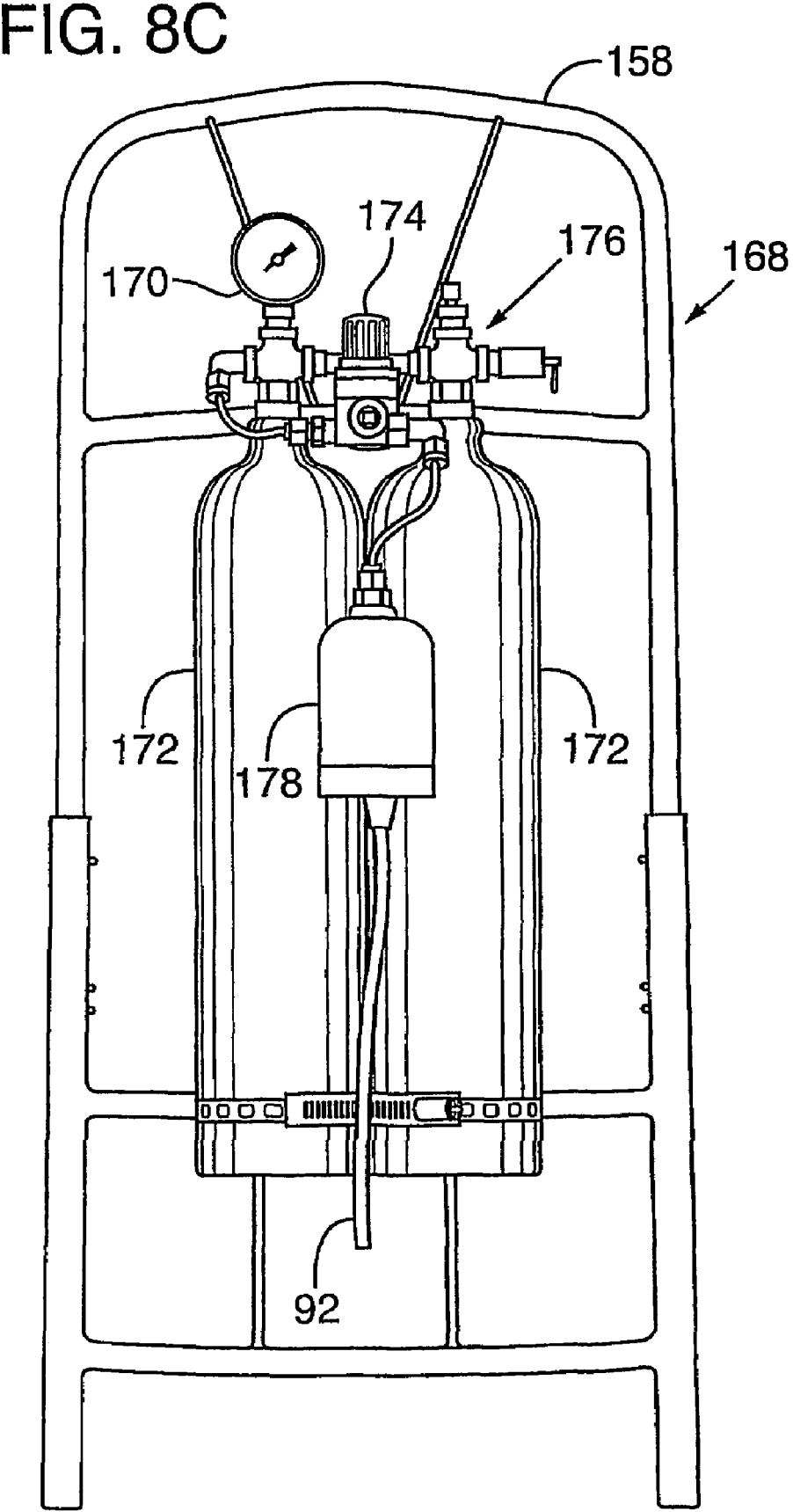

FIGS. 8A–8C show an embodiment of a jet nebulizer comprising two main parts, a backpack mounting the air supply system comprising air tanks, regulator and other fittings, and a cold box containing the nebulizer, agent, and dose controls. A simple air hose connects the two pieces of the system. To administer a dose, the user presses a plunger on the top of the cold box. The nebulizer chamber is periodically refilled by pressing a second plunger.

Refrigeration means are included in the present system, which extend the period of time between removal of agent vials from their cold storage container and loss of potency due to elevated temperature. Any means of providing refrigeration on coolant to the agent is contemplated by the present disclosure and cold packs are a preferred means.

The present disclosure also comprises dosage control. Dosage control is provided preferably by a single-handed, single-stroke trigger that actuates a dosage delivery system that dispenses a timed dose of agent. Dosage control may be effected by means of an electronic timing circuit or a pneumatic timer and an adjustable needle valve. The pneumatic timer is activated with a spring-loaded plunger, which upon compression, expels the air in the plunger shaft through a check valve. The spring causes the plunger to retract slightly, forming a vacuum in the plunger shaft, which is connected to one side of a diaphragm of a vacuum-controlled pneumatic relay. The vacuum on one side of the pneumatic relay engages a valve that allows air to pass from the air supply to the nebulizer or aerosol generator. Attached to the plunger shaft is a needle valve that allows flow to bleed back into the shaft to gradually relieve the vacuum and close the air valve controlled by the pneumatic relay. The bleed rate and plunger spring constantly control the rate at which the vacuum is relieved, which in turn determines the dosage time.

FIG. 7 depicts various combinations of the components of the present disclosure. Such embodiments and various other combinations are contemplated by the present disclosure. Such embodiments can be used as mobile aerosol vaccination systems or systems for delivery of agents.

Preferred embodiments are further disclosed in the following descriptions. FIG. 1 depicts an embodiment of an aerosol delivery system 8. The aerosol delivery system 8 includes a body, or housing, 10 and an insulated cooling receptacle 12. The receptacle 12 is connected to the body 10, with contact by the exterior surface 14 of the body 10 to the receptacle 12. The insulated receptacle 12 may be connected to the body 10 with snap fittings, adhesives, or any other detachable connection that is known by one of ordinary skill in the art. The insulated receptacle 12 may consist of any lightweight, durable material including, but not limited to, plastic, metal, composite, or a wood product.

The body 10 comprises a handle body 16 for a user to grip or to hold the aerosol delivery system 8 with one or two hands. A pump handle 18 connects to the body, and functions as a pump as one means for pressurizing the aerosol delivery system 8. The body 10 may be designed into other shapes for gripping or holding the aerosol delivery system 8 with one or two hands. The pump handle 18 also can be designed into other shapes for manually pressurizing the aerosol delivery system 8.

FIG. 2 shows a cutaway interior view of the ultrasonic aerosol delivery system 8 shown in FIG. 1. The insulated receptacle 12 contains thermal packs, also referred to herein as coolant or ice packs, 20 that can connect to the interior walls of the receptacle 12. The ice packs 20 are replaceable in the receptacle and can be reusable or disposable. The design of the ice packs 20 may include various rigid or flexible exterior surfaces for molding the ice packs 20 into a conforming shape to provide an internal chamber for receiving and holding a vial. Further, the ice packs 20 may include an external or internal continuous member that is cylindrical in form or it may include numerous external or internal members oriented to provide a relatively high surface area for the ice pack 20. Located between the ice packs 20 is the vial chamber 22. The vial chamber 22 can be cylindrically-shaped, but may be formed in other shapes in order to fit closely with the shape of a vaccine or drug vial 24.

A vial 24 is located in an inverted position within the receptacle 12, when the receptacle 12 is connected to the body 10. The vial can contain an agent or vaccine to be administered to a patient. The vial 24 is held in place by contact with the interior surface of the ice packs 20. Additionally, the vial 24 is held in place by a vent probe 26 and an agent probe 28. The agent probe 28 is a small cylindrical tube with a pointed end 30 that is used to puncture a rubber cap 32 incorporated or connected to the vial 24. Alternatively, the agent probe 28 can include other shaped tubes, including rectangular or square, that can puncture the rubber cap 32 of the vial 24.

For example, the vial 24 can be used to store a reconstituted measles vaccine. The ice packs 20 can be used to maintain the reconstituted measles vaccine at a constant temperature so that the vaccine is not adversely affected by ambient or external temperature.

The vent probe 26 can be connected to the agent probe 28 where the agent probe 28 enters the insulated receptacle 12. The vent probe 26 typically is longer, but of a similar shape as the agent probe 28. The vent probe 26 can be a hollow cylinder that connects with the hollow portion of the agent probe 28. The vent probe 26 is operable to allow air to be drawn from outside of the vial 24 to replace the volume of an agent or vaccine that is dispensed from the vial 24 via the vaccine probe 28.

The aerosol delivery system 8 includes an ultrasonic nebulizer 36 that contains a plate member or screen with numerous small holes, or orifices, with an approximate opening size of 4 to 10 microns, and more preferably 6 to 8 microns. The nebulizer may comprise a piezoelectric actuator operatively coupled to a power source. The agent probe 28 can be connected to the ultrasonic nebulizer 36 via a section of flexible tubing 38 to carry a quantity of agent from vial 24 to nebulizer 36. In operation, a user depresses a trigger and timer switch 40 connected to the ultrasonic nebulizer 36. In doing so, a signal is sent from the switch 40 to nebulizer drive electronics, or circuit, 42 connected to the ultrasonic nebulizer 36, wherein the signal can be processed. In turn, the nebulizer drive electronics 42 relays a signal to the ultrasonic nebulizer 36 to begin operation. The ultrasonic nebulizer 36 converts an agent drawn from vial 24 via the agent probe 28 into droplets of a very small size (preferably in a range of from 5 to 10 microns). Other types of nebulizers or devices that disperse an agent into a droplets of a very small size also can be used.

The aerosol delivery system 8 also includes an air control valve 44, an air reservoir 46, a mixing chamber 48, and an anti-backflow valve 50. Depression of the switch 40 opens the valve 44 which allows air stored within the air reservoir 46 to be released into the associated mixing chamber 48. The air that is expelled from the air reservoir 46 mixes with the nebulized agent in the mixing chamber 48, and opens the anti-backflow valve 50. The air and agent mixture then is free to flow past valve 50 and through a prong 54 into the naris of the patient.

The prong 54 may be of a rigid or flexible design and constructed from plastic, rubber, or other suitable material. Additionally the prong may be made of paper, with or without coating for low cost, easy disposability (as by burning), and can absorb some nasal secretions to prevent contamination. A prong can be sized in various configurations to fit into a patient's naris or as an oral prong for the mouth. The prong 54 is typically located after the mixing chamber 48 and can be removed from the aerosol delivery system 8 for replacement or disposal. Note that other types of propellants can be used, and that air is an example of a compressed gas that can be used to mix with the nebulized agent for delivery to a patient.

FIGS. 4A–4D depict various views of a prong 54 for use with an aerosol delivery system 8. The prong 54 includes an inlet channel 58, an anti-backflow valve 50, and a prong outlet 60. The anti-backflow valve 50 is located within the prong 54 and prohibits external or ambient air from flowing back into the system 8. Valve 50 includes a plurality of flexible supports, or leaf springs, 64, a valve seat, or body, 66, and conical moving valve member 68 mounted on one set of ends of supports 64. The leaf springs, or supports, 64 function to maintain the anti-backflow valve 68 in a normally open position, which allows an aerosol output stream to flow through the prong 54 and through the valve 50. After the aerosol output stream flow passes through the valve 50 and prong outlet 60, leaf springs 64 may compress and allow the moving valve 68 to seat securely against the valve body 66. The leaf springs 64 return to their starting position once air has ceased to travel into the prong exit 60. Further, the valve body 66 and the moving valve member 68 are sized so that the flow area through the major portion of the length of prong 54 remains larger than the flow area at the prong exit 60. This ensures that the anti-backflow valve 50 does not impede the flow and reduce output from the prong 54. Additionally, the prong 54 can be shaped so that a straight-line path from the prong outlet 60 through the valve 50 does not exist. The prong outlet 60 can be angled to provide a physical barrier to a straight-line flow path through the prong 54, and the design of the anti-backflow valve 50 can provide another such physical barrier.

The pneumatic trigger and timer switch 40 can be equipped with an internal timer that determines the desired time of application. For example, this may be approximately 30 seconds from the start of administration of the agent. When approximately 30 seconds has elapsed, a signal is sent from the pneumatic trigger and timer switch 40 to the nebulizer drive electronics 42. The switch 40 then closes, preventing air from leaving the air reservoir 46. The anti-backflow valve 50 returns to the closed position upon a reverse flow of air into the mixing chamber 44. The dose timing provided by the trigger and timer switch and the drive electronics may provide for variable timing of dose, including separate periods of pre-dose air flow, dose nebulization, and post-dose flushing of the prong.

Once a dose of the drug or vaccine has been administered, the air reservoir 46 is recharged using an air reservoir charging pump 72 operatively connected to pump handle 18. The air reservoir charging pump 72 is located within the housing 10 and connected to the air reservoir 46. Specifically, the air reservoir 46 is recharged by manually and repeatedly applying pressure to a charging pump handle 18 connected to the housing 10 via a pin 74.

Power used to operate the nebulizer 36 can be supplied by a rechargeable battery pack 78. The battery pack is contained within the housing 10 and is electrically connected to the pneumatic trigger and timer switch 40 and an AC power converter 80. The battery pack 78 can be recharged in several ways. First, a hand-crank dynamo 84, located at the bottom portion of the body 10, can be used to recharge battery pack 78. Second, the battery pack 78 may be recharged through the use of an AC power jack 86 in cooperation with an external power supply (not shown) and the AC power converter 80.

Figure 3:
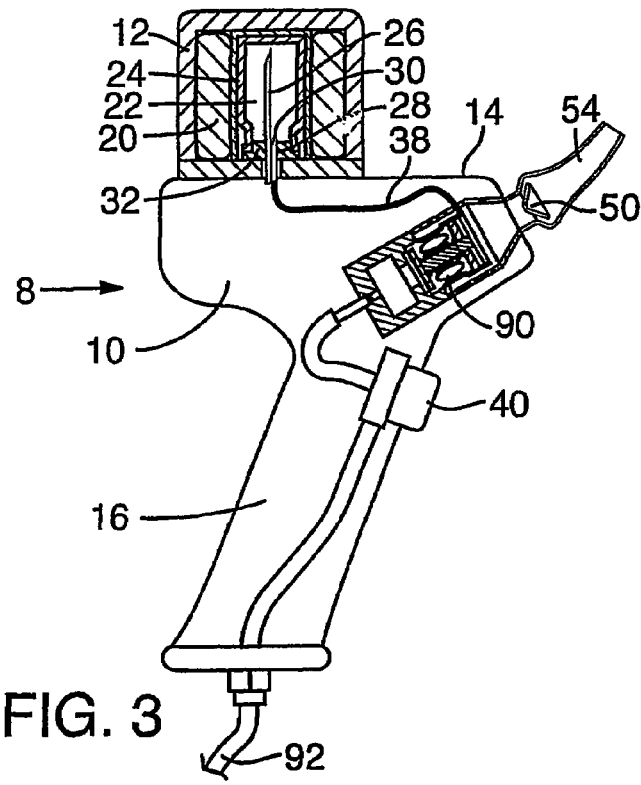
FIG. 3 shows a cutaway side view of another embodiment of the present disclosure comprising a pneumatic system.

FIG. 3 depicts an alternate embodiment, which includes a pneumatic aerosol generator delivery system or device. The embodiment shown in FIG. 3 somewhat resembles the embodiment detailed previously and shown in FIGS. 1 and 2, however, there are some differences. Here the agent contained within the vial 24 can be delivered to and nebulized with a pneumatic nebulizer 90. The pneumatic nebulizer 90 provides functions similar to and substitutes for the ultrasonic nebulizer 36 as described in FIGS. 1 and 2. An external air supply 92 connects to the pneumatic nebulizer 90 to provide an air source. The pneumatic nebulizer 90 is powered by air from the external air supply 92. The nebulized agent can be delivered to a patient after the agent has been mixed with the air from the external air source 92.

Generally, the external air source 92 can be any source of pressurized air that is external to the body 10 of the aerosol delivery system 8 and is further operable to connect to the pneumatic nebulizer 90 or other type of nebulizer. For example, the air source 92, as further described and depicted in FIG. 7, may include a hand or foot pump 96, a portable compressor 98, a stationary compressor 100, or a low pressure air tank 102 that can be recharged using either a hand or foot pump 96, a portable compressor 98, or a stationary compressor 100.

FIG. 6 depicts an orifice plate 106 of a nebulizer (for example, shown and described in FIG. 3 as 90) for an aerosol delivery system. The orifice plate 106 typically has numerous openings, or orifices, 108 of approximately 6 to 8 microns in diameter. Disposed substantially parallel to and spaced a short distance from orifice plate 108 is an actuator plate 110 with a liquid receiving chamber 112 therebetween. Aerosol droplets of the vaccine liquid are formed by a pressure pulse created by the rapid vertical reciprocation motion of an actuator 110 that forces the liquid through a multitude of small openings 108 in a microdrilled orifice plate 106. On each cycle of the actuator 110, during upward movement a series of droplets 116 are ejected from all of the openings simultaneously, then the actuator retracts (pulling in fresh fluid from a supply reservoir, or vial, through tube 38) for the next cycle. When a dose of agent is provided to the nebulizer 90, the nebulizer 90 can form voluminous amounts of small drops 116 of the agent.

FIGS. 5A–5C illustrate a pneumatic nebulizer 90 for use with an embodiment of an aerosol delivery system such as described generally with regard to FIG. 3. FIG. 5A illustrates an end, or top, view of the nebulizer, and FIG. 5B shows a side view of the nebulizer. FIG. 5C shows a cross-sectional view of the nebulizer taken generally along the line 5C—5C in FIG. 5A. The pneumatic nebulizer 90 includes a housing 120 that can be connected to a compressed air supply (shown in FIGS. 3 and 7 as 92). The pneumatic nebulizer 90 can include an inlet orifice 122, an actuator, or accumulator, chamber 124, a valve plate 126, an orifice plate 106, an impact pin 128, a spring 132, a valve plate seating surface 134, a mixture chamber 136, a diaphragm 110, and an aerosol outlet 138. The diaphragm 110 is similar to actuator 110 in FIG. 6 and in cooperation with orifice plate 106 provides a vaccine chamber 112. Air from the compressed air supply 92 is typically introduced to the nebulizer 90 through inlet orifice 122. The inlet orifice 122 leads to an actuator chamber 124 (also referred to as an accumulator volume) where the compressed air can collect within the housing 120. The valve plate 126 is seated upon seating surface 134 above the actuator chamber 124. The impact pin 128 and spring 132 are operatively interposed between the valve plate 126 and the diaphragm 110. The orifice plate 106 is located above the diaphragm 110. The spring 132 is positioned around the impact pin 128 and between the diaphragm 110 and the valve plate 126 so that a force against the valve plate 126 can compress spring 132 and push the diaphragm 110 toward orifice plate 106. An agent can be introduced into chamber 112 between the diaphragm 110 and the orifice plate 106. The mixture chamber 136 is located above the orifice plate 106 and concentrically positioned around the plates 126, 106, pin 128, and spring 132 elements. The mixture chamber 136 leads to the orifice outlet 138 which interfaces with the ambient or external air.

A support sleeve 144 having holes 146 formed therein supports orifice plate 106 and diaphragm 110 at its upper end. A guide plate 150 secured in sleeve 144 and having a central bore guides pin 128 in its vertically reciprocating motion and provides an upper support for the top end of spring 132.

When the compressed air supply 92 supplies air through the inlet orifice 122 to the actuator chamber 124, the compressed air places pressure upon valve plate 126. As the air pressure builds against the valve plate 126, eventually the pressure overcomes the force of the spring 132. At this pressure, the compressed air moves the valve plate 126 away from valve plate seating surface 134 and air passes through holes 146 and enters the mixture chamber 136. Movement of the impact pin 128 with valve plate 126 causes the diaphragm 110 to move in direct relation to the valve plate 126 and the impact pin 128. This movement forces diaphragm 110 toward orifice plate 106 to cause a portion of the agent in chamber 112 to move through the small openings (shown as 108 in FIGS. 5A and 6) within the orifice plate 106 and produces fine droplets 116 of the agent. The droplets of the agent then enter the mixing chamber 136 where the pressurized air carries the droplets toward the aerosol outlet 138. The impact pin 128 travels only a short distance before the air pressure bearing against the valve plate 126 is less than the force generated by the spring 132. As a result, the spring 132 returns the valve plate 126, the impact pin 128 and the diaphragm 110 to their respective original positions. This reciprocation cycle is repeated rapidly to produce numerous droplets of agent for administration to a patient and continues until the compressed air supply 92 is shut off.

FIGS. 8A–8C show an embodiment of a jet nebulizer aerosol delivery system with other portable accessories. Rather than mounting an insulated receptacle 12 on the exterior surface 14 of the system 8 as shown in FIGS. 1–3, a cold box 156 as shown in FIG. 8A can be used to contain a stored amount of the agent to be delivered to patients. The box further contains the nebulizer, agent and dose controls. The cold box 156 is operative to maintain the agent at a constant temperature. The box and the air supply are connected by the use of conventional flexible tubing (not shown). Additionally, the cold box 156 is designed so that it can be attached to a backpack frame 158 as shown in FIG. 8B. To administer a dose, the user presses one of plungers 162, 164 on the top of the cold box 156. The nebulizer chamber is periodically refilled by pressing the other of plungers 162, 164. The jet nebulization system may recycle a large fraction of the fluid during operation. The behavior necessitates a relatively large reservoir of fluid within the nebulizer chamber, with a minimum liquid level for effective operation.

FIG. 8C illustrates a portable air supply 168 for an aerosol delivery system. The air supply 168 includes a pressure gauge 170, one or more air tanks 172, a pressure regulator 174, a fill valve 176, and a carbon filter 178. The pressure gauge 170 connects to the air tanks 172, and displays the air pressure in the tanks 172. Further, the pressure regulator 174 connects to the air tanks 172, and limits the amount of pressure that is to be supplied to a nebulizer. The air tanks 172 can be filled with pressurized air via an associated fill valve 176. As air from the air tanks 172 is dispensed to the nebulizer, air travels from the air tanks 172 through the pressure regulator 174 and an associated carbon filter 178 to the nebulizer.

FIG. 7 shows a schematic diagram of embodiments of an aerosol delivery system including several alternative components for use in the system. An air supply 92 may include a direct, manually-operated, hand or foot pump 96, a direct, powered air source supplied by a portable compressor 98, a stationary compressor 100, or a rechargeable low-pressure air tank 102. As shown the low pressure air tank may be supplied with pressurized air by either a hand or foot pump 96, portable compressor 98, or stationary compressor 100. Additionally, cold (or thermal) packs 20 may either be reusable or disposable. Furthermore, delivery of the nebulized agent from the nebulizer 32 to a patient can be through a nasal prong 54 or an oral prong 56. Note that a variety of alternative components can comprise the present system. The components shown in FIG. 7 are by way of example, and are not intended to limit the scope of the invention.

FIGS. 9A and 9B illustrate another embodiment of an aerosol delivery system 180. It is somewhat similar to that illustrated and described in relation to FIGS. 1 and 2. It includes a body, or housing, 182 and an insulated cooling receptacle 184. The insulated receptacle 184 may be constructed as previously described in regard to the embodiment illustrated in FIGS. 1 and 2 and is capable of enclosing a vial 186 into which a vent probe 188 and agent probe 190 extend.

The aerosol delivery system 180 includes an ultrasonic nebulizer 192 that contains a plate member or screen 194 with numerous small holes, or orifices, with appropriate size openings to deliver agent as described. The agent probe 190 is connected to the ultrasonic nebulizer 192 through a tube 196 to carry a quantity of agent from vial 186 to nebulizer 192.

Figure 10:
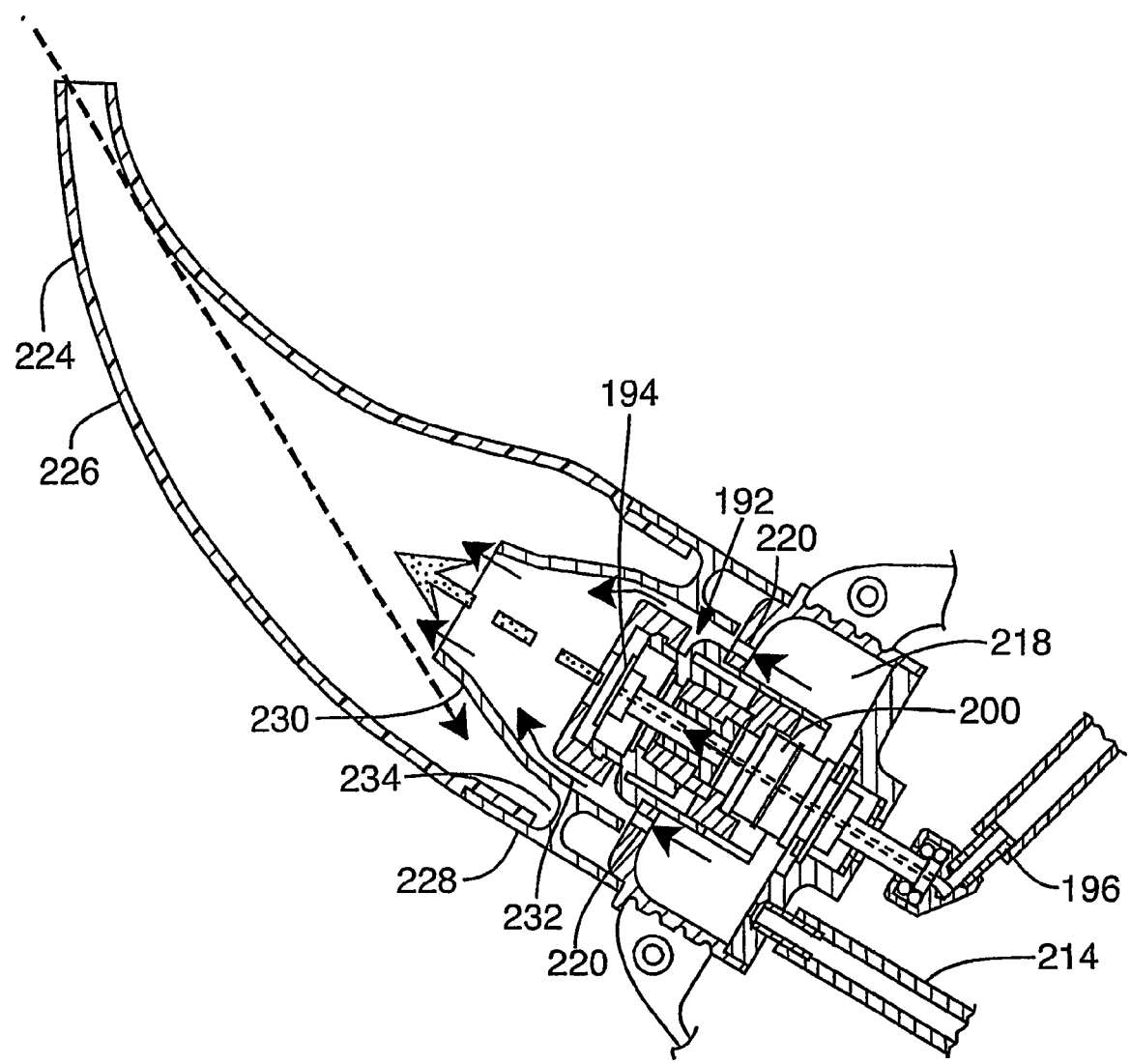
FIG. 10 is an enlarged cross-sectional view of a prong and aerosol generator used in the embodiment of FIG. 9A.

Referring to FIG. 10, the nebulizer 192 includes an orifice plate 194 and an underlying actuator plate. The orifice plate and actuator plate may be similar to those shown and described at 106, 110 in FIG. 6 with a chamber 112 therebetween into which fluid, or agent, may be drawn from vial 186. An ultrasonic element 200 is operable to vibrate the actuator plate to drive droplets of fluid, or agent, from the orifice plate as previously described.

Referring again to FIG. 9A, a battery pack 202, nebulizer electronics 204, and trigger switch 198 are operatively interconnected to each other such that pressing of trigger switch 198 actuates the nebulizer electronics to provide electrical power from the battery pack to drive the ultrasonic drive element 200.

Mounted within body 182 is an electrically operated air pump 206. An air inlet side of pump 206 is connected through a tube 208 to one side of an air filter 210. The opposite side of the filter 212 is open to atmosphere, such that air for supplying the device is drawn through filter 210 to pump 206. Another tube 214 connects the outlet side of air pump 206 to a region adjacent nebulizer 192. Referring to FIG. 10, air from the pump and tube 214 may enter an air plenum 218 surrounding the base end of nebulizer 192. Air under pressure may escape from plenum 218 through a plurality of orifices, or bores, indicated generally at 220.

The air pump also is operatively connected to the trigger switch and battery pack, such that depressing the trigger switch causes the air pump to draw air through filter 210 and discharge it through tube 214 into plenum 218. The pressurized air then escapes through orifices 220.

A nasal prong 224 is removably coupled to body 182 adjacent nebulizer 192. In the illustrated embodiment (best shown in FIG. 10) the nasal prong is formed in two pieces; a curved prong body 226 and a base, or cowl, portion 228. The body and base portions 226, 228 can be manufactured as two molded pieces that snap-fit together, with the base portion having an end that is removably received on a part of body 182. The body portion 226 is upwardly curved to produce a path which inhibits contamination of the nebulizer elements and other reusable portions of the system.

The base portion 228 includes a centrally located converging nozzle section 230, the lower end of which surrounds the orifice plate of the nebulizer. An air passage 232 is provided between nozzle section 230 and the nebulizer. Pressurized air from plenum 218 exiting through bores 220 may travel through air passage 232 and out through nozzle section 230 into prong body portion 226 to be delivered to a patient.

The base portion is designed to direct an air and aerosol stream away from the orifice plate outwardly into the prong body to be delivered to a patient. It also provides what may be termed a gutter 234 around the inner periphery of the base to collect any nasal drippings, condensation, vaccine, or other fluid for disposal with the prong.

Operation of the device illustrated in FIGS. 9A, 9B, and 10 is somewhat similar to that previously described for other embodiments. Explaining briefly, prong 224 is inserted into a patient's orifice and trigger switch 198 is depressed. This starts air pump 206 to provide air through tube 214 to plenum 218 and into the interior of nozzle section 230. Actuation of the trigger switch also initiates operation of ultrasonic nebulizer 192 which draws agent from vial 186, and ejects it in small droplets into the air stream flowing through nozzle section 230. This is carried in an air/aerosol stream outwardly into the prong to be delivered to a patient.

While various embodiments have been described above, these descriptions are given for purposes of illustration and explanation. Variations, changes, modifications and departures from the systems and methods disclosed above may be adopted without departure from the spirit and scope of this disclosure.

What is claimed is:

1. A system for administering an agent, comprising:
   a housing;
   an air source operable to provide positive pressure air;
   a nebulizer operable for receiving an agent from a vial coupled to the housing and converting the agent into an aerosolized agent;
   a mixing chamber to receive the aerosolized agent from the nebulizer and air from the air source;
   a release mechanism operable for releasing a quantity of the agent from the vial to the nebulizer, wherein the agent is converted into an aerosolized agent that is mixed with air from the air source in the mixing chamber;
   a prong with an inlet and an outlet, wherein the inlet is operable to receive the aerosolized agent and air mixture from the mixing chamber, and the outlet is operable to deliver the aerosolized agent and air mixture to a patient when the prong is inserted into a patient's orifice;
   an anti-backflow valve between the mixing chamber and the prong outlet, operable to permit flow from the mixing chamber to the prong, and to inhibit flow in a reverse direction; and
   a cooling chamber connected to the housing, the cooling chamber being adapted to receive the vial and being operable to maintain the agent at a selected temperature.

2. The system of claim 1, wherein the air source is contained within the housing.

3. The system of claim 1, which further comprises a source of electrical energy connected to the nebulizer.

4. The system of claim 1, wherein the air source comprises a compressed air chamber coupled to said housing.

5. The system of claim 1, wherein said air source comprises an external source of compressed air.

6. The system of claim 1, wherein the release mechanism comprises a manually activated trigger on said housing.

7. The system of claim 6, wherein said trigger is operatively coupled to said nebulizer and air source such that upon actuation of the trigger the nebulizer produces aerosolized agent and air under pressure is mixed with the aerosolized agent for delivery to a patient.

8. The system of claim 6 which further comprises a timing circuit, which upon activation of the trigger controls the timing of the release of agent from the vial to the nebulizer, conversion of the agent into an aerosol, mixture of the aerosolized agent with air, and delivery of the aerosolized agent and air mixture to a patient.

9. The system of claim 1, wherein the prong comprises a hollow tube configured to fit closely in a patient's naris.

10. The system of claim 1, wherein the prong comprises multiple internal channel portions in angularly disposed relation to each other so that a direct path does not exist from the prong outlet through the anti-backflow valve.

11. The system of claim 1, which further comprises an agent probe operable to extend into said vial to permit drawing the agent from the vial.

12. The system of claim 11, which further includes a vent probe capable of extending into the vial to admit air into the vial as agent is drawn therefrom via said agent probe.

13. The system of claim 1, wherein said air source comprises an air chamber within said housing.

14. The system of claim 1, wherein said air source comprises a manually actuated pump on said housing.

15. The system of claim 1, which further comprises a battery coupled to said housing and connected to the nebulizer.

16. The system of claim 15, wherein said battery is rechargeable, and said system comprises an AC power converter coupled to said housing.

17. The system of claim 15, wherein said battery is rechargeable, and which further comprises a manually actuated dynamo mounted on said housing and operatively connected to said battery for recharging the battery.

18. The system of claim 1, wherein the prong comprises an elongate tubular member having an aerosol inlet portion adjacent one of its ends and a patient engaging portion adjacent its opposite end configured to fit closely in a patient's orifice.

19. The system of claim 18, wherein said anti-backflow valve is positioned in said prong intermediate said aerosol inlet portion and patient engaging portion.

20. The system of claim 1, wherein said prong comprises a prong body and said anti-backflow valve comprises a valve seat, a valve closure member shiftable toward and away from the valve seat between closed and opened positions, and a plurality of support members operatively connecting said valve member to the prong body permitting shifting of the valve member between its opened and closed positions under the influence of the direction of air pressure imposed upon the valve member.

21. The system of claim 20, wherein said valve member is substantially conical.

22. The system of claim 20, wherein said support members comprise leaf springs.

23. The system of claim 1, wherein said nebulizer comprises an ultrasonic nebulizer.

24. The system of claim 23, wherein said ultrasonic nebulizer comprises a piezoelectric actuator operatively connected to a power source.

25. The system of claim 1, wherein said nebulizer comprises an element having a plurality of openings extending therethrough through which agent is distributed upon actuation of the nebulizer to produce droplets of agent in a size range of from 4 to 10 microns.

26. The system of claim 1, wherein the cooling chamber comprises a replaceable ice pack.

27. The system of claim 1, wherein the vial has a selected external configuration, and said cooling chamber has an internal configuration shaped to closely fit about the external configuration of said vial.

28. A system for administering an agent, comprising:
a housing
an air source operable to provide positive pressure air;
a nebulizer operable for receiving an agent from a vial coupled to the housing and converting the agent into an aerosolized agent;
a mixing chamber to receive the aerosolized agent from the nebulizer and air from the air source;
a release mechanism operable for releasing a quantity of the agent from the vial to the nebulizer, wherein the agent is converted into an aerosolized agent that is mixed with air from the air source in the mixing chamber;
a prong with an inlet and an outlet, wherein the inlet is operable to receive the aerosolized agent and air mixture from the mixing chamber, and the outlet is operable to deliver the aerosolized agent and air mixture to a patient when the prong is inserted into a patient's orifice; and
an anti-backflow valve between the mixing chamber and the prong outlet, operable to permit flow from the mixing chamber to the prong, and to inhibit flow in a reverse direction;
wherein said nebulizer comprises an element having a plurality of openings extending therethrough through which agent is distributed upon actuation of the nebulizer to produce droplets of agent in a size range of from 4 to 10 microns;
wherein said nebulizer comprises a pair of spaced apart plate members defining a liquid-receiving chamber therebetween adapted to receive a quantity of agent from the vial, one of said members having a plurality of orifices extending therethrough through which liquid may be forced from the chamber to produce droplets of agent, and the system further comprises actuating mechanism operable to reciprocate at least one of said members toward the other in a compression actuation to force liquid from said chamber through said orifices.

29. The system of claim 28, wherein said chamber is operatively coupled to said vial whereby agent may flow from said vial to the chamber, and upon movement of the elements away from their compression actuation serves to draw agent from the vial into the chamber.

30. The system of claim 28, wherein said actuating mechanism comprises an operator coupled to one of said plate members, operable to reciprocate said one plate member toward and away from the other of said plate members.

31. The system of claim 30, wherein said operator comprises a reciprocating member mounted for reciprocation toward and away from one of said plate members, such that upon extension the reciprocating member presses said one member toward the other member, and upon retraction allows said one member to move away from the other member.

32. The system of claim 31, wherein said reciprocating member comprises a fluid-actuated reciprocating piston operatively connected to said air source whereby application of positive pressure air thereto produces reciprocation of the piston to produce aerosolized agent and also to channel air into the mixing chamber to mix with the aerosolized agent.

33. The system of claim 32, which further comprises a biasing element operatively coupled to said piston to assist in reciprocation thereof.

* * * * *